(12) United States Patent
Suvee et al.

(10) Patent No.: US 8,563,072 B2
(45) Date of Patent: Oct. 22, 2013

(54) SUSPENSION CONTAINING HYDRONIUM STABILIZED COLLOIDAL SILICIC ACID NANOPARTICLES, FORMULATION OBTAINED FROM THE SAID DILUTED SUSPENSION, POWDER OBTAINED FROM THE SAID DE-HYDRATED SUSPENSION, COMPOSITIONS OBTAINED FROM THE SAID POWDER, PREPARATION AND USE

(75) Inventors: Ivo Suvee, Lima (PE); Guillaume Tourgis, Paris (FR)

(73) Assignees: Aquarius Investholding, SARL, Luxembourg (LU); Jisbrey, S.A., Montevideo (UY)

( * ) Notice: Subject to any disclaimer, the term of this patent is extended or adjusted under 35 U.S.C. 154(b) by 46 days.

(21) Appl. No.: 12/988,183

(22) PCT Filed: Apr. 16, 2009

(86) PCT No.: PCT/EP2009/054515
§ 371 (c)(1),
(2), (4) Date: Nov. 22, 2010

(87) PCT Pub. No.: WO2009/144087
PCT Pub. Date: Dec. 3, 2009

(65) Prior Publication Data
US 2011/0064798 A1 Mar. 17, 2011

(30) Foreign Application Priority Data
Apr. 17, 2008 (WO) ................. PCT/EP2008/054643

(51) Int. Cl.
| | | |
|---|---|---|
| A23L 1/30 | (2006.01) | |
| A61K 9/48 | (2006.01) | |
| A61K 33/00 | (2006.01) | |
| A01N 59/00 | (2006.01) | |
| A01N 55/00 | (2006.01) | |
| A61K 31/695 | (2006.01) | |

(52) U.S. Cl.
USPC ............. 426/648; 424/451; 424/600; 514/63

(58) Field of Classification Search
None
See application file for complete search history.

(56) References Cited

U.S. PATENT DOCUMENTS

| | | |
|---|---|---|
| 1,233,933 A | 7/1917 | Swartsfagr |
| 2,356,774 A | 8/1944 | Marshall |
| 2,391,255 A | 12/1945 | Marshall |
| 2,392,767 A | 1/1946 | Robinson, Jr. |
| 2,408,654 A | 10/1946 | Kirk |
| 2,588,389 A | 3/1952 | Iler |
| 3,083,167 A | 3/1963 | Shannon |
| 3,867,304 A | 2/1975 | Mindick et al. |
| 4,037,019 A | 7/1977 | Steger |
| 6,335,457 B1 | 1/2002 | Seguin et al. |
| 2006/0099276 A1 | 5/2006 | Vanden Berghe |
| 2006/0142465 A1* | 6/2006 | Carr et al. ..................... 524/493 |
| 2006/0178268 A1 | 8/2006 | Kros |
| 2007/0238088 A1* | 10/2007 | Rubinsztajn et al. ............. 435/4 |
| 2008/0069753 A1* | 3/2008 | Floess et al. .................. 423/335 |

FOREIGN PATENT DOCUMENTS

| | | | | |
|---|---|---|---|---|
| BE | EP1110909 | * | 6/2001 | ............. C01B 33/12 |
| EP | 0743922 B1 | | 7/1998 | |
| EP | 1110909 A1 | | 6/2001 | |
| WO | 02051748 A1 | | 7/2002 | |
| WO | 03101915 A1 | | 12/2003 | |

* cited by examiner

Primary Examiner — Sean Basquill
(74) Attorney, Agent, or Firm — Kenyon & Kenyon LLP

(57) ABSTRACT

The present invention relates to hydronium stabilized silicic acid nanoparticles, to the formulation obtained from the said diluted suspension, to the powder obtained from the said dehydrated suspension and to the preparation or dosage form obtained from the said suspension, formulation or powder, to their preparation and their use in all kinds of applications in the domains of food, medicine, pharmaceutics, cosmetics. The present invention provides a stable suspension of colloidal silicic acid nanoparticles having a pH lower than 0.9, a molar silicon concentration between 0.035 and 0.65, a free water concentration of at least 30% (w/v) and a ratio between hydronium ion and Si molar concentrations higher than 2 and preferably inferior to 4. The present invention further provides a method for preparing a stable suspension of colloidal silicic acid nanoparticles, which comprises the steps of providing an aqueous inorganic or organic silicon solution and quick mixing said aqueous inorganic or organic silicon solution with water containing a strong acidic compound at a temperature inferior at 30° C., preferably comprised between 1 and 25° C., to form a suspension of colloidal silicic acid nanoparticles having a pH lower than 0.9, stabilized by hydronium ions, the ratio between hydronium ions and Si molar concentrations being higher than 2 and preferably inferior to 4, for a molar silicon concentration between 0.035 and 0.65 and a free water concentration of at least 30% (w/v).

34 Claims, No Drawings

US 8,563,072 B2

SUSPENSION CONTAINING HYDRONIUM STABILIZED COLLOIDAL SILICIC ACID NANOPARTICLES, FORMULATION OBTAINED FROM THE SAID DILUTED SUSPENSION, POWDER OBTAINED FROM THE SAID DE-HYDRATED SUSPENSION, COMPOSITIONS OBTAINED FROM THE SAID POWDER, PREPARATION AND USE

This is a 371 national phase application of PCT/EP2009/054515 filed 16 Apr. 2009, claiming priority to PCT/EP2008/054643 filed 17 Apr. 2008, the contents of which are incorporated herein by reference.

FIELD OF THE INVENTION

The present invention relates to a stable aqueous suspension, containing hydronium stabilized silicic acid colloidal nanoparticles able to dissolve in aqueous environments, to their preparation and use. It relates also to the solid compound of the said suspension, under the form of powder, to its preparation and uses. It relates further to various compositions containing the said powder and to their uses. The powder keeps the bio-availibity of the aqueous suspension.

BACKGROUND OF THE INVENTION

Silicates are abundant as silicates and alumino silicates. They make up nearly all the earth's crust. Many organisms use silica as protecting or fortification material against predators, infection or extreme environmental conditions. Silica can also participate in metazoan development and may influence enzymatic reactions.

Specific bacteria, protozoa, algae and plants make certain silica structures. They use silicon anions, silicate complexes or mono silicic acid to create specific silica (polymerized) structures, which are normally used as protecting shell layer. Some sponges form spicules allowing anchoring. They make therefore a differentiated cell type producing scaffolding silicatein proteins. Diatoms which are important in the biogenic silicon cycle form silicate frustules as protecting layer against predators.

Silicon is found in plants at concentrations ranging from 0.01 to 10% or more (dry weight basis). This is much higher than most macro nutrients. Multiple studies demonstrated the role of silicon as an alleviator of biotic and abiotic stress induced by other organisms (bacteria, fungi, viruses, protozoa, insects, . . . ) and s physical conditions (salt stress, drought stress, water stress, heat stress, osmotic stress, cold stress, etc . . . ). Different parts of the plant may show large variations in silicon uptake. Silica phytoliths are observed in the cell walls or lumina of plant cells. There are also associations visible with cell wall components (polysaccharides, pectins, lignins, proteins, etc . . . ). Non polymerized silica as mono and disilicic acid, the precursors of biogenic silica, may also play an active role in certain enzymatic systems involved in oxidative stress and in the biosynthesis and metabolism of certain macro molecules important in biochemical pathways (ref. 22, 23).

Humans are continuously exposed to different sources of silicon as dust (silica, silicates), soil particles (silicates, silica) dissolved silica in water, health products, inert silicon dioxide in pharmaceuticals and cosmetics, organic silicon compounds in medical implants and devices, dietary additives (inert silicates), dietary supplements (colloidal gels, dissoluble organic silicon compounds), plant extracts (phytolytic), cosmetics and toiletries (insoluble silicates), detergents, etc. Typically none of these products are highly bioavailable. Only dissoluble silica and mono or disilicic acid in drinking water and in food or dietary supplements are bioavailable and safe for human. Most silicon compounds are taken up by diet and drinking water. The dietary intake in a Western diet is about 15-60 mg Si/day. Higher consumption of plants results in a higher intake up to 200 mg Si/day. Beer also is an interesting source of bio available silicon.

The gastro intestinal absorption of silicon depends mainly on the presence of absorbable species of silicic acid and silicates. Only soluble silicates (or silicate complexes) and mono- or disilicic acid from dissolution of silica compounds are readily absorbed and excreted.

Moreover, silicon is still a risk factor in human diseases (ref. 24, 25, 26, 27, 28). More specifically crystalline (sands) or amorphous (natural or synthetic) silica is active through macrophage activation and release of cytokines, growth factors and oxidants (ROS). Some concerns have even been expressed on a possible association between silica and esophageal cancer. It is therefore important to produce a silica sol compound which is soluble, hydrated and preferably quickly dissoluble upon dilution. Stable and purified synthetic sol particles could be harmful. Soluble silica compounds are not at all toxic. Crystalline silica may release free radicals in solution (ROS) in combination with soluble iron and may damage so directly the epithelial cell layer. It is important that the stabilizing agent is able to scavenge the ROS radicals, which are also inducing polymerization. It is therefore crucial not to use dried or evaporated silica which dissolutes very slowly.

Silicon is not yet recognized as an essential element although it is essential for specific bacteria, fungi, diatoms and plants related to survival and replication. is Silicon plays also an important role in the growth and strength of animals and humans. Silicon is strongly related to the development of connective tissue and the activity of cells present in the extra cellular matrix and could play an important therapeutic role in the maintenance and prevention or treatment of extra cellular matrix related diseases such as arteriosclerosis, arthritis, osteoarthritis, osteoporosis, skin—hair and nail diseases, reduced mineralization of bone, reduced collagen synthesis, reduced skeleton growth, joint diseases, healing of fractures, etc. . . . It is also important in detoxification of aluminum ions and other toxic metals. Several recent publications show the importance of silicon in bone health and especially in the synthesis of collagen. It is therefore important to have access to an acceptable technology and a formulation of bio available silicon for plants, animals and humans.

The following patents: U.S. Pat. Nos. 1,233,933, 3,867, 304, WO02/051748, U.S. Pat. Nos. 2,356,774, 2,391,255 and 3,083,167 deal with silica sol formation in acid medium. These documents disclose silica sols stabilized by means of ionic transfer or by use of organic silicic acid complexing compounds.

Many silicic acid compositions have been proposed as silicon suppletion products for plants, animals and humans, but they deal with non colloidal silicon or with non stabilized monosilicic acid.

U.S. Pat. No. 4,037,019 discloses acidic hydrosols and process for coating therewith. Metal silicates or hydrous magnesium silicate and optionally a magnesium compound and a boron compound are mixed in acidic medium. The obtained sols are resistant for at least 15-20 minutes. This invention describes mixtures of silicate (solid powders) which are not at all soluble in acidic medium.

U.S. Pat. No. 6,335,457 describes a complex containing biologically assimilable orthosilicic acid, wherein orthosilicic acid is complexed with a polypeptide and under solid, stable and concentrated form. Alcohol is used during the synthesis of the solid form and the pH is between 1.5 and 4 during the preparation. No silicic acid colloids are disclosed.

EP-743.922 describes the preparation of ortho silicic acid (monomer) stabilized with a quaternary ammonium compound by dissolving a silicon compound in the solution containing the stabilizing agent. Silicon molar concentrations higher than 1.4 are obtained at values under pH 4. No colloidal silicon is formed. The stabilizer must always be present and cannot be omitted.

US-2006/0178268 teaches an aqueous solution containing boric acid and non-colloidal silicic acid. Boron is present during hydrolysis of the silicon compound in an acidic solution. Boric acid absorbs to the oligomers. Without the presence of a humectant at a high concentration only very low silica (up to 0.0035 mol) and boron concentrations can be obtained. Boron is needed for stabilization of non colloidal oligomers and for the much higher biological activity. Without boron and the humectants the stability is lost at higher molar silicon concentrations at pH values below 2. The small oligomers are not retained on a MW 20.000 filter or filters with higher cut off. Humectants include urea, dextran, polysorbate, glycol, sorbitol, galactose, cellulose, vegetable gum. They must be used at concentrations higher than 30% (W/V). Boron free solutions could not be obtained by this formulation.

US-2006/099276 describes a method for the preparation of silicic acid comprising extrudate, said extrudate, its use and a pharmaceutical composition comprising the said extrudate. An extrudate of stabilized silicic acid as mono silicic acid or its oligomers is proposed. These compounds are formed in the presence of quaternary ammonium compounds, amino acids or an amino acid source and mixed with a carrier. This mixture is extruded and dried before use. Mono silicic acid and oligomers up to 40 units could be present at maximum 1.25 mol Si. Pellets are the final result. $^{29}$Si NMR shows Q0 and Q1 peaks, characteristic for mono and disilicic acid.

EP-1.110.909 describes a method for preparing ortho- or mono silicic acid starting from an acid hydrolysable compound in the presence of a solvent agent in order to prevent polymerization into oligomers and colloidal silica. The solvents for stabilization are glycols, glycerol, DMSO, polysorbate 80 and polyglycols. Mono silicic acid is made in situ. The silicon concentration is in the range of 0.01 to 50% (W/V). Silicic acid remains in its monomeric form. All examples mentioned are performed with glycerol as solvent. The solvent cannot be removed anymore (high boiling temperature).

U.S. Pat. No. 2,588,389 provides processes for production of silicic acid sols in which silicic acid has a low molecular weight and not greater than the silicate used during preparation. The solution is added to an aqueous acidic solution (pH 0.5-4 or pH 1-3) containing insoluble cation-exchangers. After addition the pH may not exceed 4. After filtration the pH is about 2-3.

U.S. Pat. No. 2,392,767 relates to the production of low molecular weight silicic acid forming complexes with an organic hydrogen bonder. The bonder is extracted by means of a solvent. The pH is between 1.6 and 3.

U.S. Pat. No. 2,408,654 relates to silicic acid sols and the process for producing silicic acid together with an organic hydrogen bonding donor (ether). The pH is variable and such that the corresponding metal silicate is not formed. The original silicic acid sol has a pH of 2.

There is still a need to produce and stabilize, for longer periods, silicic acid particles in aqueous solutions, which are able to quickly dissolve into the bioavailable forms of silicon, the mono and disilicic acids, upon dilution in an aqueous environment. Such sols are also more important than mono- or di-silicic acid in detoxification reaction of heavy metals.

Silica is ubiquitous in nature. Its precursor molecules (silicate anion, mono and disilicic acid) are present in water at low concentrations. These forms are taken up by plants and all other organisms. Silica particles formed after polymerization under natural pH conditions are negatively charged and interact with all kind of cells in the environment. Very slow dissolution of these particles finally results in mono silicic acid which is taken up by the plant cells or other organisms.

It is generally accepted that polymerization of monosilicic acid occurs at pH values under 7 through formation of siloxane bonds resulting in dimers, trimers, tetramers and larger oligomers. These mostly cyclic oligomers assemble very quickly into large fibrils and form a three-dimensional open network which results by further associations in gel formation. The oligomers show Ångstrom (Å) dimensions (non colloidal) and subsequent small sols or nano-particles which assemble in nanometer and micrometer fibrils or particles before gel formation. Primary sol particles are formed after active polymerization of hundreds of oligomers (colloidal). Once sol particles are formed it is difficult to inhibit further association and polymerization of these particles into larger particles and fibril associations (micrometer sols).

The silicate anion shows different structures: linear, planar, cyclic and three dimensional. Silicon nuclear magnetic resonance (NMR) spectroscopy provides a basic method for characterizing silicate anion mixtures. It uses the relationship between the silicon atom and its neighbors, counting the number of other silicon atoms to which atom it is connected to through an oxygen atom (Q0, Q1, Q2, Q3 and Q4). Q0: monomeric (no connections) is typical for mono silicate and Q4 is typical for all atoms in the interior of polymeric colloidal silica (ref. 29, 30, 31, 32, 33, 34, 35).

Colloidal silica shows no Q0 and Q1 peaks but heterogeneous and multiple Q3 and Q4 peaks. Oligomeric structures show distinct homogeneous Q1, Q2 and Q3 peaks. The ratios between the Qs are also different in oligomeric and colloidal silicic acid. Mono acid ($H_4SiO_4$) and disilicic acid ($H_6Si_2O_7$) show the same peak characteristics as the mono and disilicate ions.

Mono silicic acid is normally neutral and relatively inert to physical conditions. It may easily cross different membrane structures. Silicate complexes and silica species (negatively loaded) react more on the different mucus layers in the intestines.

There are practically no extensive studies concerning sol and gel formation from monosilicic acid and oligomers at pH values under 1, starting from solutions of inorganic or organic silicon compounds. There are a lot of studies dealing with the formation of silica sol with the intention to make different kinds of gels. Silica sol-gel experiments with different water, silicon and proton concentrations were mainly prepared to study the effect on the gelling time, pore size and characteristics of the gel. (ref. 1 to 20). It was demonstrated that at pH values below the point of zero charge (pH 2) and more specifically at pH values inferior to 1 that the gelation time decreases and sol-gels are formed quite rapidly (ref. 21). Surprisingly, the applicants discovered that only in this low pH region, nano particles of silicic acid are formed and stabilized, under specific conditions, under the form of a colloidal suspension which is stable for several days or weeks. Moreover surprisingly the applicants discovered that only this suspension could further be stabilized with aqueous stabilizers for long periods, particularly several weeks, months or years, at ambiant temperature.

Colloidal silica nano particles for industrial use are normally stabilized after purification between pH 2 and 9. At the end of the preparation stabilized concentrated (superior to 0.7 mol Si) and desalted sols are mostly proposed. The situation under pH 2 and more precisely under pH 0.9 is not fully documented. It is proposed that dimeric silicic acid forms quickly siloxane bonds resulting finally in gelation under pH 0.9 because the polymerization time decreases (rate increases) very quickly under pH 2. It is also known that the addition of salts or peroxides ($H_2O_2$ precursors of reactive oxygen species), induces polymerization.

SUMMARY OF THE INVENTION

The present invention relates to hydronium stabilized silicic acid nanoparticles, to the formulation obtained from the said diluted suspension, to the powder obtained from the said dehydrated suspension and to the preparation or dosage form obtained from the said suspension, formulation or powder, to their preparation and their use in all kinds of applications in the domains of food, medicine, pharmaceutics, cosmetics.

The present invention provides a stable suspension of colloidal silicic acid nanoparticles having a pH lower than 0.9, a molar silicon concentration between 0.035 and 0.65, a free water concentration of at least 30% (w/v) and a ratio between hydronium ion and Si molar concentrations higher than 2 and preferably inferior to 4. The present invention further provides a method for preparing a stable suspension of colloidal silicic acid nanoparticles, which comprises the steps of providing an aqueous inorganic or organic silicon solution and quick mixing said aqueous inorganic or organic silicon solution with water containing a strong acidic compound at a temperature inferior at 30° C., preferably comprised between 1 and 25° C., to form a suspension of colloidal silicic acid nanoparticles having a pH lower than 0.9, stabilized by hydronium ions, the ratio between hydronium ions and Si molar concentrations being higher than 2 and preferably inferior to 4, for a molar silicon concentration between 0.035 and 0.65 and a free water concentration of at least 30% (w/v).

DETAILED DESCRIPTION

The first aim of the present invention is to synthesize de novo silicic acid nanoparticles, stable and able to dissolve quickly into monosilicic and disilicic acid (bio available silicon) upon dilution in aqueous environment. Surprisingly, it was found that the preparation of such stabilized suspensions under strict final hydronium ion, silicon, water and salt concentrations is only possible under pH 0.9 and silicon molar concentrations between 0.035 and 0.65.

The applicants have carefully studied the formation of silicic acid under strong acidic conditions in water starting from inorganic or water hydrolysable organic silicon compounds. So they discovered the existence of small colloidal particles which pass through a 0.1 micron filter, which are not filterable on a MW 20.000 filter and which are stable without adding any stabilizing compound (liquid or solid compound). The experiments were performed under strict conditions of pH and silicon concentration. The stabilization was done by hydronium ions at pH conditions under 0.9 and silicon molar concentrations between 0.035 and 0.65. The temperature is preferably between 1° C. and 25° C. The colloid is formed during the first hours and might be further stabilized for 12 hours at low temperature. It is stable for days, weeks or months depending on the silicon concentration and the temperature. The free water (non-hydronium, or pure, solute-free water) concentration is minimal 30% (w/v). A such minimal concentration of 30% is considered as necessary to avoid the eventual phenomenous of polymerisation due to evaporation and/or to attraction of water by the added compounds as below mentioned, especially humectants ou waterbinding products, for instance salts. The molar silicon concentration must never be higher 0.65 in spite of evaporation for stability reasons.

The suspension of the present invention can be easily dissolved in an aqueous environment. The standard dissolution test was performed with 0.3 molar concentration of silicon by a 50 fold dilution at pH above 3 in water. Quick dissolution occurs after a few hours at pH 4 and 30° C., after 30 minutes at pH 4 and 37° C. and at pH 6.5 and 30° C. Instant dissolution occurs at pH above 8.

Very small arrow peaks Q0 of monosilicic and/or Q1 of disilicic acid are seen in the $^{29}$Si NMR of the obtained solution when using the highest Si concentrations while Q2, Q3 & Q4 peaks gradually disappear in function of time. Moreover the presence of monosilicic and/or disilicic acid in the obtained solution can be demonstrated with the molybdenum blue method. These observations show well that the dissolution of the colloidal suspension of the present invention in an aqueous environment leads to the liberation of monosilicic and/or disilicic acid in the obtained solution.

According to a first aspect, the present invention provides a stable suspension of colloidal silicic acid nanoparticles having a pH lower than 0.9, a molar silicon concentration between 0.035 and 0.65, a free water concentration of at least 30% (w/v) and a ratio between hydronium ion and Si molar concentrations higher than 2 and preferably inferior to 4.

Stabilization of this suspension is at least 3-6 weeks at room temperature for a molar silicon concentration of 0.2 and 6-12 weeks at temperatures under 6° C. This corresponds to the period of time during which a visual observation of the suspension shows it is clear (transparent).

The $^{29}$Si NMR of the suspension shows a typical colloidal silica spectrum with:
  no Q0 and Q1 peaks for mono silicic acid and disilicic acid;
  separated low Q2 peak, mostly between 5 and 10% of total peak area;
  heterogeneous peak domains around Q3 and Q4.

Other properties of the suspension according to the invention are listed below:
  A yellow complex is formed with $H_2O_2$ (at concentration of $H_2O_2$ above 0.02%).
  Source of monosilicic and/or disilicic acid upon dilution (the presence of which can be demonstrated with the molybdenum blue method)
  Highly bio available upon dilution for plants, animals and humans.
  Gel formation after addition of certain humectants as glycerol, mono- and disaccharides, polysaccharides, polysorbates, etc. in concentrations above 10% (w/v) and incubation at room temperature.
  Gel formation upon evaporation or drying with loss of more than 20% water.
  Useful as aluminum neutralizer.
  Only high concentrations (molar concentration superior to 3) of monovalent alkali metals cations destabilize the colloidal suspension in contrast with sol formation at higher pH values.

According to another aspect, the present invention further provides a method for preparing a stable suspension of colloidal silicic acid nanoparticles, which has a final molar silicon concentration Y comprised between 0.035 and 0.65, the method comprising the steps of:

providing an aqueous inorganic or organic silicon solution having a molar silicon of 2Y;

diluting quickly two times the said aqueous inorganic or organic silicon solution in adding it in a aqueous acid solution of which the amount of acid is determinated in order to obtain an acidified Y solution having a pH lower than 0.9 and a ratio between hydronium ions and Si molar concentrations being higher than 2;

stirring, during or after the addition, until obtaining the stable suspension of colloidal silicic acid nanoparticles.

This suspension is prepared after titration and calculation of the needed stabilizing hydronium concentration. Mono silicic acid and its oligomers polymerize into nano silicic acid particles until stabilization by hydronium ions and do not grow further. They are quickly dissoluble upon dilution.

The inorganic silicon solution can be an aqueous inorganic alkaline solution. In this case, the method comprises the following steps:
a) Providing an aqueous inorganic alkaline solution,
b) Determination of the final molar silicon concentration Y,
c) Diluting the alkaline solution, as much as possible in purified water, resulting in a molar silicon concentration of 2Y and preferably at temperature <30 C
d) Titration of the amount of acid needed to neutralize the diluted solution to pH 7.0
e) Calculating the amount of acid needed to further achieve a pH lower than 0.9 and to reach the ratio of 2 between the molar concentration of hydronium ions and silicon.
f) Making an appropriate acidified aqueous solution and,
g) mixing quickly the diluted solution into the appropriate acidified solution until obtaining the said stable colloidal suspension of silicic acid nanoparticles.

The organic silicon solution can be prepared starting from an organic silicon compound. In this case, the method comprises the following steps:
a) Providing an organic silicon compound,
b) Determination of the final molar silicon concentration Y,
c) Taking a volume of the compound to be diluted in acidified water resulting in a silicon concentration of 2Y molar,
d) Adding slowly the volume of the compound under stirring and/or sonication into acidified water at pH 0.9 and continuing until complete hydrolysis,
e) Diluting the obtained solution two times under stirring and/or sonication with acidified water containing the supplementary acid to reach the ratio between hydrogen ions and silicon molar concentrations, the pH of this solution staying lower than 0.9, until obtaining the said stable colloidal suspension of silicic acid nanoparticles.

During the acidification strong mineral acids are used such as HCl, $H_3PO_4$, $H_2SO_4$, $HNO_3$. Most preferably HCl and $HNO_3$ are used.

Completely solubilized silicates or silicon salts are used as inorganic silicon compounds.

Organic silicon solutions used are aqueous solutions of hydrolysable organic silicon compounds, most preferably alkoxy silanes or alkylesters of mono silicic acid ($Si(OR)_4$), $Si(OR)_3OH$, $Si(OR)_2(OH)_2$, $SiOR(OH)_3$ in which R is a lower alkyl compound $C_1$-$C_4$, preferably $C_2H_5$. The hydrolysis of the organic compound leads to formation of ROH. The titration of ROH allows to follow the evolution of the hydrolysis.

In a preferred embodiment of the present invention, the stable suspension of colloidal silicic acid nanoparticles is further stabilized for longer periods of time, particularly longer than 4 weeks, by addition to said suspension of a primary stabilizer which is an organic sulfur compound, for instance such as MSM (methylsulfonylmethane) or DMSO (dimethylsulfoxide), in concentrations varying from 0.01 to 25% (w/v).

Stabilization of the colloid suspension for longer periods can also be obtained by adding a secondary stabilizer showing the following characteristics: good water solubility, strong hydronium attracting, and neutralizer of ROS (reactive oxygen species) inducing polymerization.

However, the usual humectants as mono- and polysaccharides (glycerol, lactose, maltose, dextrose, sucrose, sorbitol, xylitol, glucose, dextran, cellulose, cellulose derivates, glucans, starch, pectines, alginates, proteins or hydrolysates, polysorbate) are not useful as secondary stabilizer for the suspension according to the invention. Indeed, they induce on the contrary aggregation of the colloidal particles into gel formation.

The case of the present invention is completely different to the stabilization of monomeric silicic acid and oligomers previously described. Colloidal silicic acid forms nano particles while mono silicic acid and oligomers are Ångstrom sized. Inhibition of colloidal silicon formation in the latter preparations can therefore only be successful when the humectants are already present at high concentrations during the preparation and hydrolysis of the precursor, resulting in a complexation with monomeric silicic acid or oligomers.

Stabilization of colloidal silicic acid according to the invention is performed through attraction of the hydronium ions surrounding the silicic acid coils or spheres and inhibiting condensation of the nano particles into bigger sols and gel formation. These newly described colloids do not show Q0 and Q1 peaks in $^{29}Si$ NMR while Q2 is present. This spectrum resembles biogenic silica but the particles are much more dissoluble. Broad multiple peaks are seen in the Q3 and Q4 region. Usually, monosilicic and disilicic acid show always very narrow peaks Q0 and Q1 and their oligomers show distinct narrow Q1, Q2 and Q3 peaks and combinations thereof and a minor Q4 peak.

Dissolution of the present colloidal suspension occurs quickly, compared with other industrial sols, after dilution and at pH equal or superior to 3. $^{29}Si$ NMR of the dissoluted solution shows clearly a narrow Q0 and Q1 peak, typical of monosilicic acid and disilicic acid, at high silicon concentrations, but the molybdenum blue method is more appropriate for detection of these two silicic acids.

Moreover, the stable suspension of colloidal silicic acid nanoparticles is further stabilized for longer periods (more than a year) by the addition of a secondary stabilizer, which, as indicated above, is a strong hydronium attracting substance, soluble in water and preferably selected from the chemical group glycol (propylene glycol, etc.) poly-ether compounds (polyethylene glycols)), sulphated polysaccharides, polymers of carboxylic acid and hydroxyl acids or combinations thereof.

With such secondary stabilizers, the stable suspension acquires resistance against strong polymerization inducers such as peroxides ($H_2O_2$, peracetic acid and mono persulfates, etc) and high mineral concentrations (salts of Calcium, Magnesium, Strontium, Iron, Cobalt, Boron, Copper, Zinc, etc.).

Addition of molybdate to this stable suspension results in a typical marine blue coloration for the mono silicic acid complex formation only after more than 1 year at room temperature.

The secondary stabilizer is present in concentrations ranging from 0.5% (w/v) to 60% (w/v), most preferably between 20 and 50% (w/v).

The combination of a primary and secondary stabilizers may lower the concentration of the secondary stabilizer.

The addition of such hydronium attractants results in an increased stability of the colloidal suspension for more than 3 years at 4° C. and more than 2 years at 37° C.

This suspension is also stable after addition of hydrogen peroxide which normally induces sol and gel formation. Up to 2.5% hydrogen peroxide could be combined with 0.18 mol Si and results in a stable suspension for 1 year at 25° C.

The suspension of the present invention quickly dissolves upon dilution in water or an aqueous solution into monosilicic and disilicic acid at pH between 2.5 and 9.5 and forms water insoluble precipitations or gel by reduction of the water content to a final free water content lower than 20% (w/v). This suspension is completely filterable on 0.1 micron filter (more than 98% filterable Si) and non filterable on a MW 20.000 filter (less than 20% filterable Si).

Thus, the present invention describes for the first time a preparation of bio-available colloidal silicic acid prepared at pH lower than 0.9 and limited in silicon concentration. This colloidal suspension is stable for some time and further stabilized by the addition of a primary stabilizer, such as MSM, or a second organic stabilizer for longer periods up to more than one year at room temperature. A mixture of both kinds of stabilizers results in longer stabilization.

The pH of the suspension of the present invention must always be less than 0.9, included when it contains other compounds such as the stabilizers above-mentioned and/or other sources and/or nutrients as below mentioned. In presence of stabilizers, nutrients or other compounds may be added more easily. A lot of additions may increase the pH value, but the pH must never be higher than 0.9 after such addition for stability reasons.

Upon dilution of the suspension in an aqueous medium the bio-available compounds of mono and/or disilicic acid are gradually formed.

Examples of suspension of colloidal silicic acid nanoparticles:

1. 500 ml aqueous potassium silicate solution containing 1.4% silicon (w/v) (0.5M Si) was mixed into an equal volume of an aqueous 5% hydrochloric acid solution (about 1.65M hydronium ion) within one minute under strong stirring. The pH of the obtained suspension is under 0.9. This suspension is stable for at least 1 week at 20° C. or 4 weeks at 4° C.
2. 500 ml aqueous potassium silicate solution containing 1.4% silicon (w/v) (0.5M Si) was mixed into an equal volume of an aqueous 8% nitric acid solution (about 1.72M hydronium ion) within one minute under strong stirring. The pH of the obtained suspension is inferior to 0.9. This suspension is stable for at least 1 week at 20° C. or 4 weeks at 4° C.
3. The suspension prepared as described in example 1 was supplemented with 12% MSM one hour after the mixing. This suspension was stored at 15° C. for 3 months without loss of stability (no gel formation).
4. 250 ml aqueous potassium silicate solution containing 2.8% silicon (w/v) (1M Si) was mixed into an equal volume of an aqueous 10% hydrochloric acid solution (about 3.3M hydronium ion) under strong stirring. After one hour the suspension obtained was diluted with an equal volume of polyethylene glycol 400 as stabilizing agent. The pH of the obtained suspension was under 0.9. This suspension was stable for at least 2 years at 25° C. and 3 years at 4° C.
5. The suspension prepared and stabilized as described in example 4 was supplemented with 0.5% calcium (w/v) as calcium chloride, 0.5% magnesium (w/v) as magnesium chloride, 0.5% zinc (w/v) as zinc chloride and 0.2% selenium (w/v) as selenate. This suspension shows the same stability after addition of these salts as the one prepared and stabilized as prescribed in example 4.
6. The suspension prepared and stabilized as described in example 4 is supplemented with 1% copper (w/v) as copper chloride and stored at 25° C. during one year without loss of stability.
7. The suspension prepared and stabilized as described in example 4 was supplemented with 0.5% taurine (w/v). This suspension was stored at 25° C. during 2 years without loss of stability.
8. The suspension prepared and stabilized as described in example 4 was supplemented with 1% L-threonine (w/v) and stored at 4° C. during 18 months. This suspension shows no loss of stability.
9. The suspension prepared and stabilized as described in example 4 was supplemented with 0.05% lycopene (w/v) and stored at 20° C. during one year, without loss of stability and without loss of antimicrobial activity.
10. 250 ml aqueous potassium silicate solution containing 2.8% silicon (1M Si) was mixed very quickly into an equal volume of an aqueous 16% nitric acid solution (about 3.5M hydronium ion) under strong stirring. After one hour the suspension was diluted with an equal volume of polyethylene glycol 200 as stabilizing agent. The pH of this suspension was under 0.9. This suspension is stable for at least 2 years at 25° C.
11. The suspension prepared and stabilized as described in example 10 was supplemented with 0.5% taurine (w/v) and 0.01% folic acid (w/v) and kept at 4° C. during one year. The solution shows no loss of stability.
12. 250 ml aqueous potassium silicate solution containing 2.8% silicon (1M Si) was mixed very quickly into an equal volume of an aqueous 10% hydrochloric acid solution (3.3M hydronium ion) under strong stirring. After one hour the suspension was diluted with an equal volume of propylene glycol as stabilizing agent. The suspension was stable for at least 2 years at 25° C.
13. The suspension prepared and stabilized as described in example 12 was supplemented with 0.3% calcium (w/v) as calcium chloride, 0.3% magnesium (w/v) as magnesium chloride, 0.5% zinc (w/v) as zinc chloride and 0.1% selenium (w/v) as selenate. The suspension was stored at 4° C. for 2 years showing no loss of stability.
14. 250 ml aqueous potassium silicate solution containing 2.8% silicon (1M Si) was mixed very quickly into an equal volume of an aqueous 16% nitric acid solution (3.5M hydronium ion) under strong stirring. After one hour the suspension was diluted with an equal volume of propylene glycol as stabilizing agent. This suspension was stable for at least 2 years at 25° C.
15. The suspension prepared and stabilized as described in example 14 was supplemented with 1% L-lysine (w/v) and 1% sodium citrate (w/v) and stored at 25° C. After one year the solution showed no loss of stability.
16. The suspension prepared and stabilized as described in example 1 was diluted one hundred fold in tap water and supplemented with an equal volume of an aqueous silicate solution containing 0.005% Si resulting in a bio available silicon formulation.
17. The suspension prepared and stabilized as described in example 4 was diluted in the drinking water for a first group of pigs during their growth period. The dilution grade was adapted every week to the mean weight of the animals. The useful concentration was 4 mg Si/50 kg body weight/day. A second control group of pigs received a drinking water no supplemented with the said suspension. After 6 months of cultivation the pigs were slaughtered and similar samples of their meat were analyzed for global fatty acid composition. Fatty acid analysis demonstrated increased omega 3 fatty acid concentrations in the first group of pig supplemented with silicon of the suspension of colloidal silicic acid nanoparticles. The ratio omega 6/omega 3 fatty acids decreased from 11.2 to 3.8 in the first silicon treated group of pigs.

The hydronium stabilized suspension according to the invention is used as source of bio-available silicon for microorganisms, plants, animals and humans as such in:

All kind of waters (tap, drinking water for humans and animals, mineral, distilled, process, reversed osmosis, rain, fortified, river, ocean, soil, filtered, cooling water, aqueous solutions, suspensions, emulsions and combinations thereof),
Biological preparations,
Plant fertilizers,
Feed additives for animals,
Food and food supplements, namely dietary food supplements for human consumption,
Nutritional products,
Nutritional meal replacement supplements,
Nutritional drink mixes,
All kind of beverages,
Nutraceuticals,
Vitamin and mineral preparations,
Nutritional pills in the nature of nutritional supplement,
Nutritional additives for use in foods,
Food and food products,
Medical foods, baby foods and geriatric foods,
Food for medically restricted diets,
Drugs,
Cosmoceuticals and as additive therein,
Cosmetics, topical and personal care products,
Pharmaceutical compounds and their different compositions,
Combination with other compounds such as anti-oxidants, enzyme inhibitors, hormones, etc.
Combination with different sources (salts, oxides, complexes, etc . . . ) of Ca, K, Na, Mg, Mn, B, Li, Sr, Se, Mo, Fe, Co, Cu, Zn, Ti, Al, Ag, Cr, Si, P, S, N, F, Cl, Br, I.
Combination with nutrients such as sugars, fats, proteins, protein hydrolysates, nucleic acids, vitamins, amino acids, plant extracts, biological macro molecules, primary and secondary plant metabolites, compounds of biological pathways and combinations thereof.

The hydronium stabilized suspension is also used for anti-corrosive applications as such or in combination with molybdates or other anti-corrosive compounds upon dilution.

According to another aspect, the present invention further provides formulations of the diluted hydronium stabilized suspension, used as food supplement, nutraceutical, feed additive, pharmaceutical preparation, topical formulation, hygienic formulation, concentrated fertilizer and growth regulator, concentrated plant protection formulation, concentrated bio-available silicon formulation to induce biological processes in plans, animals, humans and micro-organisms. Use of these formulations in drinking water of animals and humans or as plant fertilizer with the aim to increase the concentration of omega 3 fatty acids in these organisms, compared to formulation-free controls.

According to another aspect, the present invention provides a soluble powder which contains bio-available silicon and a method for preparing the said powder, starting of the stable suspension above disclosed.

The method is characterized by the following steps a) adding a highly water soluble carrier to the stable suspension of colloidal silicic acid nanoparticles having a pH lower than 0.9, a molar silicon concentration between 0.035 and 0.65, a free water concentration of at least 30% (w/v) and a ratio between hydronium ion and Si molar concentrations higher than 2 in order that the carrier absorbs the colloidal silicic acid nanoparticles and b) evaporating the free water until obtaining a powder.

The evaporation is made without using any solvent

Thus, a special preparation starting from the silicic acid hydronium stabilized suspension or from the suspension with the primary stabilizer results in a powder which contains bio-available silicic acid after addition of a carrier attracting, precipitating and protecting the silicic acid colloid during evaporation, particularly under vacuum.

Amino acids, proteins or polyamins generally do not stabilize the aqueous colloidal silicic acid suspension at pH less than 1.5 for longer periods. Therefore, they are not used as primary or secondary stabilizers. Surprisingly, addition of a polyamine, protein or protein hydrolysate carrier to the silicic acid suspension at pH less than 0.9 and at a high concentration (more or equal 2% w/v) followed by quick evaporation of this suspension, results in a dry and water soluble powder. The evaporation can be performed by different quick evaporation techniques (quick removal of free water), but preferably by the technique of freeze-drying after freezing the protein or a protein hydrolysate carrier containing suspension.

It must be underlined that the evaporation of the colloidal silicic acid suspension prepared without the carrier as control always results in an insoluble silicic acid precipitation Nevertheless, addition of high concentrated polyamine, protein or protein hydrolysate may also cause solubility problems at such low pH and may also, during evaporation proteins, stick on to surfaces (glass, plastic or metal). Surprisingly, addition of the primary stabilizer, particularly methylsulfonylmethane MSM, together with the polyamine—preferably with a molecular weight lower than 300,000—, protein or protein hydrolysate resolves the solubility problems and results in a more homogenous and easier to remove powder. Therefore the preferred method to prepare the concentrated silicic acid powder consists of the addition of the carrier (polyamine, protein or protein hydrolysate) together with the primary stabilizer, particularly methylsulfonylmethane MSM at concentrations between 0.01% and 20% (w/v). The carrier concentration in the aqueous suspension is preferably between 2% and 20% (w/v). The colloidal silicic acid structures are precipitated on the carrier during evaporation without formation of insoluble polymers.

Such powder containing a high silicon concentration (between 0.1% and 15%) can be used as food supplement or food or feed additives. The powder is completely soluble in purified water. For instance, 50 mg of the powder, obtained starting from the hydronium stabilized suspension pH<0.9, using a quick evaporation process and diluted in 10 ml purified water, results in a clear solution with a pH between 1.5 and 3.

The protein or protein hydrolysate are purified from plants (peas, bean, cereals, nuts, seeds, soy, rye, rice . . . ) or from animal origin (collagen or collagen hydrolysate), such as chicken, pig, calf, cow or fish.

The 29Si NMR spectrum of the powder is similar to that of the colloidal silicic acid suspension.

The hydronium stabilized suspension according to the invention, the formulation obtained upon dilution of the said suspension and the powder obtained from the said dehydrated suspension can be supplemented with:

i—Micro- and macro nutrients such as:
A) soluble salts and sources of macro- and micro and trace elements, different sources (salts, acids, oxides, complexes, etc . . . ) of Ca, K, Na, Mg, Mn, B, Li, Sr, Se, Mo, Fe, Co, Cu, Zn, Ti, Al, Ag, Cr, Si, P, S, N, F, Cl, Br, I or mixtures thereof.
B) nutrients such as sugars, fats, proteins, nucleic acids, vitamins, amino acids, plant extracts, biological macro molecules, primary and secondary plant metabolites, compounds of biological pathways and combinations thereof, or mixtures thereof;

ii—growth activators, fertilizers, biological active compounds for crop production and protection.

iii—hydrophilic and hydrophobic anti-oxidants such as carotenoids, flavonoids, accepted food additives, antioxidative enzymes, lipoic acid, . . .

iv—enzyme inhibitors, hormones, antibiotics, or other pharmaceuticals v—natural and synthetic food colorants, food sweeteners and food flavourings or mixtures thereof.

Examples of Powder Containing Bio-available Silicon

1. A white power contains 5.4% Si (w/w) as colloidal silicic acid and 71% bovine skin collagen hydrolysate. The preparation of the colloidal suspension started with alkaline potassium silicate. Freeze drying technique as evaporation technique was used
2. A white power contains 3.2% Si (w/w) as colloidal silicic acid, 52% fish collagen hydrolysate and 32% MSM. The preparation of the colloidal suspension started with alkaline potassium silicate. Freeze drying technique as evaporation technique was used
3. A white power contains 5.4% Si (w/w) as colloidal silicic, 60% pork collagen hydrolysate and 18% MSM. The preparation of the colloidal suspension started with alkaline potassium silicate. Freeze drying technique as evaporation technique was used
4. A white power contains 1.5% Si (w/w) as colloidal silicic, 52% chicken collagen hydrolysate, 10% MSM and 1% Zinc chloride. The preparation of the colloidal suspension started with alkaline potassium silicate. Freeze drying technique as evaporation technique was used.
5. A white power contains 5.4% Si (w/w) as colloidal silicic, 62% fish collagen hydrolysate, 12% MSM and 0.5% OPC (oligomers pro-anthocyanides). The preparation of the colloidal suspension started with alkaline potassium silicate. Freeze drying technique as evaporation technique was used.

50 mg of the powder of the above examples is completely solubilized in 10 ml purified water.

According to another aspect, the present invention provides preparations or dosage forms containing the powder, the formulation or the suspension of the present invention supplemented as above mentioned.

Preparations or dosage forms can be oral dosage forms such as capsule, powder, solution, suspension, tablet, lozenge, film, softgel, pill, or can be rectal dosage forms such as enema, suppository, or can be topical dosage forms such as cream, ointment, gel, paste, powder, liniment, lotion, patch, plaster or can be pharmaceutical forms such as ampule, capsule, cream, elixir, emulsion, grain, drop, spray, powder, suspension, syrup, tablet, ointment.

The preferred preparation or dosage forms are:
galenic forms: capsule, softgel, compressed lozenge, tablet, suppository, gelatin coated pill,
topical galenic or cosmetic forms: cream, gel, lotion, ointment, liminent,
medical forms: plaster, unguent, patch, gel.

For instance, the oral dosage form for food supplement is a capsule containing the powder of the present invention and further nutrients such as sugars, fats, proteins, nucleic acids, vitamins, amino acids, plant extracts, biological macro molecules, primary and secondary plant metabolites, compounds of biological pathways (glucosamine, chondroitin, hyaluronic acid, carnitine, organic acids, acetyl compounds, . . . ) and combinations thereof, or mixtures thereof.

Examples of Preparation for Food Supplements, as Capsule Containing Powder

1. A capsule contains 200 mg of the powder described in example 2 above-mentioned, 200 mg chondrotin sulfate and 400 mg glucosamine sulfate
2. A capsule contains 200 mg of the powder described in example 2, 100 mg hyaluronic acid, 3 mg boron as boron citrate, 10 mg Zinc as Zinc citrate, 100 mg alpha lipoic acid.
3. A capsule contains 150 mg of the powder described in example 2, 100 mg hyaluronic acid, 200 mg MSM, 100 mg bromelain, 3 mg boron as boron citrate and 2 mg manganese as manganese citrate.
4. A capsule contains 250 mg of the powder described in example 2, 50 microgram vitamin K2, 200 microgram folic acid and 100 mg OPC.
5. A capsule contains 150 mg of the powder described in example 2, 100 mg vitamin C (as calcium ascorbate), 200 microgram biotin, 150 mg resveratrol and 100 microgram selenium as selenate.
6. A capsule contains 150 mg of the powder described in example 2 and 500 mg type II chicken collagen.

The suspension containing Hydronium stabilized colloidal silicic acid nanoparticles of the present invention, the formulation obtained from the said diluted suspension, the powder obtained from the said dehydrated suspension and the preparation or dosage form obtained from the said suspension, formulation or powder can be used in all kinds of applications in the domains of food, medicine, pharmaceutics, cosmetics.

The invention claimed is:
1. A stable suspension of colloidal silicic acid nanoparticles having a pH lower than 0.9, a molar silicon concentration between 0.035 and 0.65, a free water concentration of at least 30% (w/v) and a ratio between hydronium ion and Si molar concentrations higher than 2, wherein said nanoparticles are soluble in water, more than 98% of the suspension passes through a 0.1 micron filter but is not filterable on a MW 20.000 filter, and $^{29}$Si NMR for the suspension shows a typical colloidal silica spectrum with a separated low Q2 peak further supplemented with at least one of the following:
i—micro- and macro nutrients
ii—growth activators, fertilizers, biological active compounds for crop production and protection;
iii—hydrophilic and hydrophobic anti-oxidants
iv—enzyme inhibitors, hormones, antibiotics, or other pharmaceuticals; or
v—natural and synthetic food colorants, food sweeteners, food emulgators and food flavourings;
or mixtures thereof.

2. A suspension according to claim 1, further comprising an organic sulfur compound as stabilizer, in concentrations varying from 0.01 to 25% (w/v).

3. A suspension according to claim 1, further comprising a secondary stabilizer showing the following characteristics:

good water solubility, strong hydronium attracting, and neutralizer of ROS (reactive oxygen species) inducing polymerization.

4. A suspension according to claim 3 wherein the secondary stabilizer, present in concentrations ranging from 0.5% (w/v) to 60% (w/v), is selected from the chemical group glycol poly-ether compounds, sulfated polysaccharides, polymers of carboxylic acid and hydroxyl acids or combinations thereof.

5. A formulation obtained by dilution in an aqueous environment of the suspension according to claim 1 comprising monosilicic acid and/or disilicic acid.

6. A method for preparing a stable suspension of colloidal silicic acid nanoparticles according to claim 1, which has a final molar silicon concentration Y comprised between 0.035 and 0.65, the method comprising the steps of:
  providing an aqueous inorganic or organic silicon solution having a molar silicon of 2Y;
  diluting two times the said aqueous inorganic or organic silicon solution in adding it in a aqueous acid solution of which the amount of acid is determinated in order to obtain an acidified Y solution having a pH lower than 0.9 and a ratio between hydronium ions and Si molar concentrations being at least 2;
  stirring, during or after the addition, until obtaining the stable suspension of colloidal silicic acid nanoparticles.

7. The method according to claim 6 comprising the following steps:
  a) Providing an aqueous inorganic strong alkaline solution,
  b) Determination of the final molar silicon concentration Y
  c) Diluting the alkaline solution, in purified water, resulting in a molar silicon concentration of 2Y and at a temperature <30 C
  d) Titration of the amount of acid needed to neutralize the diluted solution to pH 7.0
  e) Calculating the amount of acid needed to further achieve a pH lower than 0.9 and to reach the ratio of at least 2 between the molar concentration of hydronium ions and silicon;
  f) Making an appropriate acidified aqueous solution and,
  g) Mixing quickly the diluted solution into the appropriate acidified solution until obtaining the said stable colloidal suspension of silicic acid nanoparticles.

8. The method according to claim 6 comprising the following steps:
  a) Providing an organic silicon compound,
  b) Determination of the desired final molar silicon concentration Y,
  c) Taking a volume of the compound to be diluted in acidified water resulting in a silicon concentration of 2Y molar,
  d) Adding slowly the volume of the compound under stirring and/or sonication into acidified water at pH 0.9 and continuing until complete hydrolysis,
  e) Diluting the obtained solution two times under stirring with acidified water containing the supplementary acid to reach the ratio between hydrogen ions and silicon molar concentrations, the pH of this solution staying lower than 0.9, until obtaining the said stable colloidal suspension of silicic acid nanoparticles.

9. The method according to claim 6 in which strong mineral acids used are selected from the group consisting of: $HCl$, $H_3PO_4$, $H_2SO_4$ and $HNO_3$.

10. The method according to claim 7 in which completely solubilized silicates or silicon salts are used as inorganic silicon compounds.

11. The method according to claim 8 in which organic silicon solutions used are aqueous solutions of hydrolysable organic silicon compounds, selected from the group consisting of alkoxy silanes or alkylesters of mono silicic acid ($Si(OR)_4$), $Si(OR)_3OH$, $Si(OR)_2(OH)_2$, $SiOR(OH)_3$ in which R is a lower alkyl compound.

12. The method according to claim 6 comprising a step of addition to the said suspension of a primary stabilizer which is an organic sulfur compound selected from the group consisting of MSM (methylsulfonylmethane) or DMSO (dimethylsulfoxide), in concentrations varying from 0.01 to 25% (w/v), particularly in order to obtain a suspension of colloidal silicic acid nanoparticles stabilized for periods of time of at least 4 weeks.

13. The method according to claim 6 comprising a step of addition of a secondary stabilizer, which is a strong hydronium attracting substance, soluble in water selected from the chemical group glycol, propylene glycol, poly-ether compounds, sulphated polysaccharides, polymers of carboxylic acid and hydroxyl acids or combinations thereof, in order to obtain a suspension of colloidal silicic acid nanoparticles stabilized for periods more than a year.

14. A method for preparing a formulation comprising monosilicic acid and/or disilicic acid comprising the step of dissolving in water or aqueous solution the suspension according to claim 1.

15. The stable suspension according to claim 1 for use as source of mono- and di-silicic acid for micro-organisms, plants or animals.

16. The suspension according to claim 1 for use in a medical treatment as source of mono and di-silicic acid.

17. The stable suspension according to claim 1, for use in anticorrosive applications as such or in combination with molybdates or other anti-corrosive compounds upon dilution.

18. A food supplement, nutraceutical, food additive, pharmaceutical preparation, topical formulation, hygienic formulation, concentrated fertilizer and growth regulator, or concentrated plant protection formulation, concentrated bioavailable silicon formulation to induce biological processes in plants, animals, humans and micro-organisms comprising the formulation according to claim 1.

19. The formulation according claim 5 for use in a medical treatment as concentrated bio-available silicon formulation.

20. The formulation according to claim 5 for use to supplement the drinking water of animals or as a fertilizer for plants to increase the concentration of omega 3 fatty acids in the animals or plants.

21. The formulation according to claim 5 for use in a drinking water of humans so as to increase the concentration of omega 3 fatty acids in human organism.

22. A method for preparing a soluble powder containing bio-available silicon, starting with the stable suspension according to claim 1, comprising the following steps:
  a) adding a highly water soluble carrier to the stable suspension of colloidal silicic acid nanoparticles having a pH lower than 0.9, a molar silicon concentration between 0.035 and 0.65, a free water concentration of at least 30% (w/v) and a ratio between hydronium ion and Si molar concentrations higher than 2 in order to absorb and precipitate the colloidal silicic acid nanoparticles and
  b) evaporating the free water until obtaining a powder.

23. The method according to claim 22 comprising the step of adding the carrier which comprises the methylsulfonylmethane (MSM) in order to increase the solubilisation of the carrier, preferably up to concentrations of 20% (w/v).

24. The method according to claim 22 wherein the carrier is a protein, polypeptide, protein hydrolysate, a polyamine with a molecular weight lower than 300,000—or mixtures thereof.

25. The method according to claim 22 wherein the carrier is added slowly to the silicic acid suspension under stirring until complete solubilisation of the carrier at a final concentration higher than 2% (w/v), in that the pH is eventually corrected until being less than 0.9, in that the suspension obtained is stabilizated during some hours and in that the free-water of the suspension is evaporated by a quick dehydration technique, such as vacuum evaporation or freeze-drying until obtaining the soluble powder.

26. Powder containing colloidal silicic acid nanoparticles, prepared by the method of claim 22, having a silicon concentration between 0.05% and 15% (w/w).

27. The powder according to claim 26 containing from 1.5% to 8% (w/w) Si as colloidal silicic acid, from 50% to 75% (w/w) collagen hydrolysate and from 10% to 35% (w/w) methylsulfonylmethane (MSM).

28. The powder according to claim 26 further containing at least one of the following:
   i—micro- and macro nutrients selected from the group consisting of:
   A) soluble salts and sources of macro- and micro and trace elements, of Ca, K, Na, Mg, Mn, B, Li, Sr, Se, Mo, Fe, Co, Cu, Zn, Ti, Al, Ag, Cr, Si, P, S, N, F, Cl, Br, I or mixtures thereof;
   B) nutrients: sugars, fats, proteins, nucleic acids, vitamins, amino acids, plant extracts, glucosamine, chondroitin, hyaluronic acid, carnitine, organic acids, acetyl compounds, . . . and combinations thereof, or mixtures thereof;
   ii—growth activators, fertilizers, biological active compounds for crop production and protection;
   iii—hydrophilic and hydrophobic anti-oxidants carotenoids, beta-carotene, lutein, lycopene, zeaxanthin, . . . , flavonoids quercetin, hesperetin, luteolin, rutin . . . , accepted food additives, antioxidative enzymes, phenolic acids, lipoic acid, Co-Q10
   iv—enzyme inhibitors, hormones, antibiotics, or other pharmaceuticals; or
   v—natural and synthetic food colorants, food sweeteners, food emulgators and food flavourings;
   or mixtures thereof.

29. A dosage form containing a suspension according to claim 1 or a formulation or powder obtained from a suspension.

30. A dosage form according to claim 29 as capsule, softgel, compressed lozenge, tablet, suppository, gelatin coated pill, cream, gel, lotion, ointment, liminent, plaster, unguent, patch.

31. The suspension according to claim 2, further comprising MSM (dimethylsulfonylmethane) as stablilizer.

32. The suspension according to claim 4, wherein the secondary stabilizer is present in concentrations ranging from 20 to 50% (w/v).

33. The suspension according to claim 4, wherein the secondary stabilizer is PEG.

34. The suspension according to claim 1, wherein
   i) the micro- and macro nutrients are selected from the group consisting of soluble salts and sources of macro- and micro and trace elements, sources, salts, oxides, and complexes of Ca, K, Na, Mg, Mn, B, Li, Sr, Se, Mo, Fe, Co, Cu, Zn, Ti, Al, Ag, Cr, Si, P, S, N, F, Cl, Br, I and mixtures thereof, and nutrients selected from the group consisting of sugars, fats, proteins, nucleic acids, vitamins, amino acids, plant extracts, glucosamine, chondroitin, hyaluronic acid, carnitine, organic acids, acetyl compounds, and combinations thereof, or mixtures thereof; and
   2) the hydrophilic and hydrophobic anti-oxidants are selected from the group consisting of carotenoids, beta-carotene, lutein, lycopene, zeaxanthin, flavonoids, quercetin, hesperetin, luteolin, rutin, accepted food additives, antioxidative enzymes, phenolic acids, lipoic acid, Co-Q10.

* * * * *